United States Patent [19]

Balazs et al.

[11] Patent Number: 5,266,563
[45] Date of Patent: *Nov. 30, 1993

[54] HYAKYRIBATE-POLY (ETHYLENE OXIDE) MIXTURES

[75] Inventors: Endre A. Balazs, Ft. Lee; Adolf Leshchiner, Fairview, both of N.J.

[73] Assignee: Biomatrix, Inc., Ridgefield, N.J.

[*] Notice: The portion of the term of this patent subsequent to Dec. 16, 2005 has been disclaimed.

[21] Appl. No.: 464,583

[22] Filed: Jan. 11, 1990

Related U.S. Application Data

[63] Continuation of Ser. No. 256,251, Oct. 6, 1988, abandoned, which is a continuation of Ser. No. 940,624, Dec. 11, 1986, abandoned, which is a continuation-in-part of Ser. No. 619,534, Jun. 11, 1984, abandoned.

[51] Int. Cl.$^5$ .......................... A61K 7/15; A61K 7/48; A61K 31/70
[52] U.S. Cl. ........................ 514/42; 424/63; 424/64; 424/70; 424/73; 514/844; 514/846; 514/912; 514/914
[58] Field of Search .............. 424/78; 514/42, 912

[56] References Cited

U.S. PATENT DOCUMENTS

| | | | |
|---|---|---|---|
| 2,965,678 | 12/1960 | Sundber et al. | 424/341 |
| 4,141,973 | 2/1979 | Balass | 424/180 |
| 4,192,862 | 3/1980 | Pengills | 424/47 |
| 4,474,811 | 10/1984 | Masuda et al. | 424/361 |

FOREIGN PATENT DOCUMENTS

| | | | |
|---|---|---|---|
| 183717 | 11/1982 | Japan | 424/180 |
| 185208 | 11/1982 | Japan | 424/180 |
| 212300 | 12/1982 | Japan | 424/180 |

OTHER PUBLICATIONS

Schmolka, Amer. Perf. & Cosm; Jul. 1967, vol. 82, pp. 25-27, 29, 30, 54, & 55.
Chem. Abs., vol. 99, pp. 10689q, 1983.
Chem. Abs vol. 98, pp. 78155x, Shiseido, 1983.
Chem Abs., vol. 100, pp. 73782z, Pola Lab, 1984 Hoshizaki Sadao et al, 1983, Journ. Soc. Cos. Chem. Japan 17(1) pp. 19-26 (Eng).
Chem. Abs., vol. 94, pp. 109091x, Pola Chem.
Chem Abs., vol. 98, pp. 59757d, Shiseid, 1983.

*Primary Examiner*—Dale R. Obe
*Attorney, Agent, or Firm*—Sheldon Palmer

[57] ABSTRACT

Disclosed are water based, viscoelastic compositions comprising a mixture of high molecular weights hyaluronic acid salts and water soluble poly(ethylene oxides). Also disclosed are cosmetic formulations including said compositions.

8 Claims, 2 Drawing Sheets

HYAKYRIBATE-POLY (ETHYLENE OXIDE) MIXTURES

CROSS-REFERENCE TO RELATED APPLICATIONS

This application is a continuation of application Ser. No. 07/256,251, filed Oct. 6, 1988, which was a continuation of Ser. No. 940,264, filed Dec. 11, 1986, which is a continuation-in-part of application Ser. No. 619,534, filed Jun. 11, 1984, all abandoned.

BACKGROUND OF THE INVENTION

1. Field of the Invention

The present invention relates to hyaluronate based compositions, and more particularly, to such compositions, including, in addition to hyaluronate, a high molecular weight poly (ethylene oxide) and which are superior to those of our above noted co-pending application in one or more properties. The invention also relates to cosmetic formulations comprising such compositions.

2. The Prior Art

Hyaluronic acid (hereinafter referred to as "HA") as well as its salts, such as sodium hyaluronate and other alkali metal and alkaline earth metal salts (hereinafter referred to as "NaHA") is a known, naturally occurring high viscosity glycosaminoglycan having alternating $\beta$1-3 glucuronidic and $\beta$1-4 glucosaminidic bonds. The molecular weight of this material is generally within the range of 50,000 to 8,000,000 (although there are reports of HA having molecular weights as high as 13,000,000) depending on the source, method of isolation and method of determination. It is found in animal tissue, e.g. in umbilical cord, vitreous human, synovial fluid, rooster combs, group A and C hemolytic streptococci and in skin.

The isolation and characterization of HA is described in Meyer et al, J. Biol. Chem. 107, 629 (1934); J. Biol. Chem. 114, 689 (1936); Balazs Fed. Proc. 17, 1086 (1958); Laurent et al; Biochim. Biophys. Acta 42, 476 (1960). The structure of HA was elucidated by Weissman et al, J. Am. Chem. Soc. 76, 1753 (1954) and Meyer, Fed. Proc. 17, 1075 (1958).

For certain uses, extremely pure HA preparations are required; see, for example Balazs U.S. Pat. No. 4,141,973, which describes the preparation and use of such an HA.

Hyaluronate has also been known to be used in various cosmetic formulations; see, e.g. the prior art of record in parent application Ser. No. 619,534, filed Jun. 11, 1984, now abandoned.

Poly(ethylene oxides) are known water soluble non-ionic homopolymers of ethylene oxide having molecular weights up to 5,000,000. Aqueous solutions of these polymers are highly viscoelastic and are known to be used in many areas including adhesives, lubricating agents, coatings, cosmetics, etc.

Poly(ethylene oxide) is also known to form strong association complexes with a large number of other materials, such as urea, phenolics, poly(acrylic acid), etc. The reaction products formed between poly(ethylene oxide) and polymeric polycarboxylic acids are insoluble in hot and cold water (U.S. Pat. No. 3,387,061).

Poly(ethylene oxide) is known to be used in cosmetics. See, e.g., U.S. Pat. Nos. 2,991,229; 3,783,872; 3,811,349 and 4,192,862.

SUMMARY OF THE INVENTION

Figure 1:
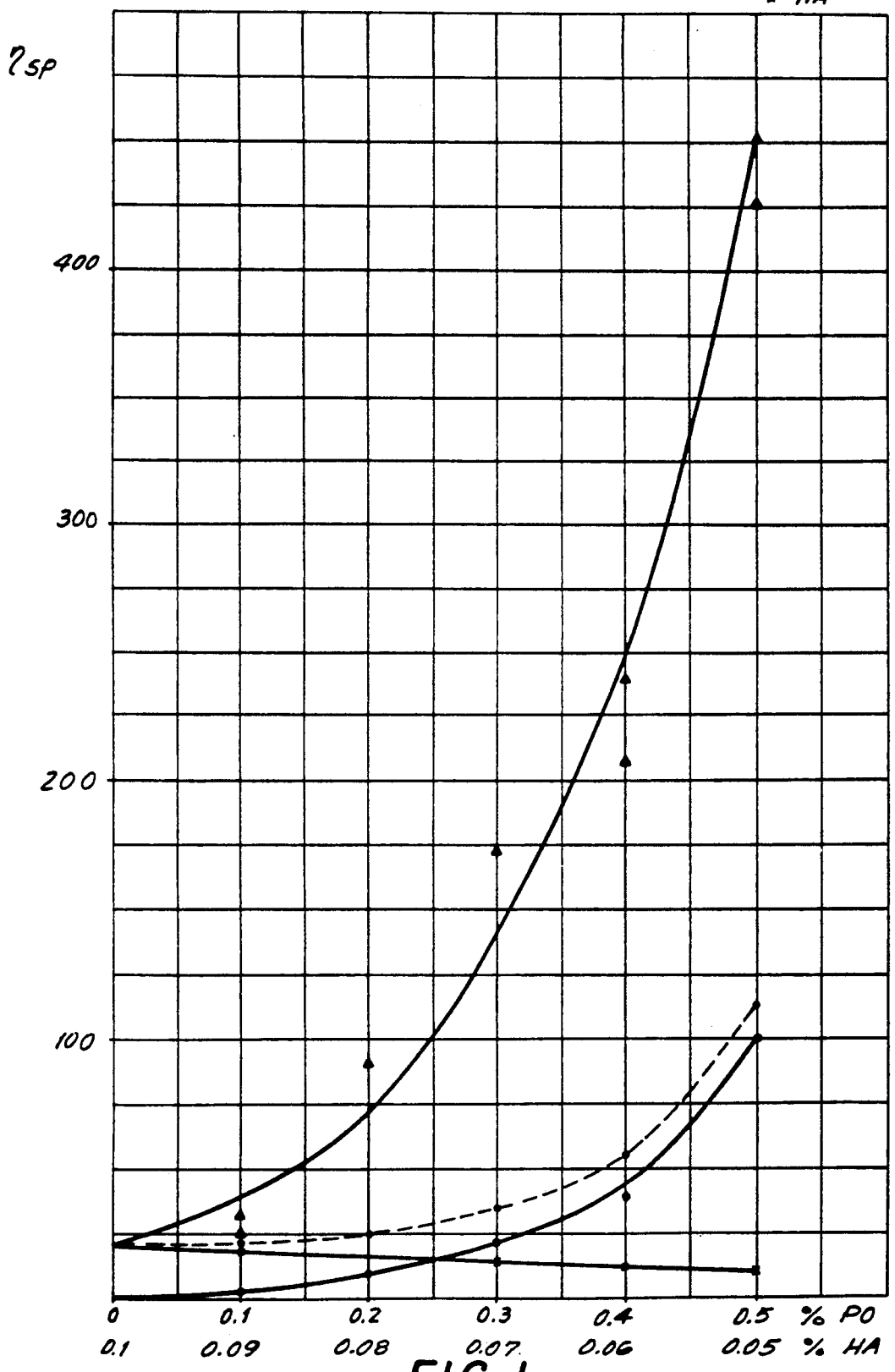
FIG. 1 is a graph showing the specific viscosity of various mixtures of a poly(ethylene oxide) and sodium hyaluronate described in examples 1-5.

Water based, highly viscoelastic substances are very useful in cosmetic formulations because they impart to such formulations a smooth, silky texture which is desirable both in terms of the function and aesthetic appeal of cosmetics.

One such substance is Hyladerm ® (Biomatrix, Inc.) which is described in U.S. Pat. No. 4,303,676. These hyaluronate compositions are expensive and thus, the art has been seeking ways to easily provide such substances at relatively low cost.

While U.S. Pat. No. 3,387,061 suggests that the reaction products of a poly(ethylene oxide) and polymeric polycarboxylic acids are water insoluble, we found, quite unexpectedly and described in parent application Ser. No. 619,534, filed Jun. 11, 1984, now abandoned, that when aqueous solutions of a hyaluronic acid salt and a high molecular weight poly(ethylene oxide) are mixed together, no water insoluble products are formed, even though hyaluronic acid is a polymeric polycarboxylic acid. Instead, what is observed is a highly viscoelastic substance in which the viscosity of the mixture is substantially in excess of the sum of the individual viscosities of the hyaluronate and the poly(ethylene oxide). This wholly unexpected property makes the resulting mixtures particularly well suited for use in cosmetic formulations both because of the desirability of the vastly increased viscosity and the reduced cost of the substance as compared with a like amount of hyaluronate composition without the poly(ethylene oxide).

It has now been found that the degree of interaction between the two polymers (HA and Polyox) does not really depend upon the molecular weight of the sodium hyaluronate. Thus, in parent application Ser. No. 619,534, filed Jun. 11, 1984, now abandoned, the lower limit of the molecular weight of the poly(ethylene oxide) was set at about $1 \times 10^6$ for the reason that a Polyox of lower molecular weight tended to form unusable precipitates when mixed with the sodium hyaluronates used therein, i.e., those with molecular weights of about $2-5 \times 10^6$. We have now found that compositions having the desired properties can be obtained over a much wider range of molecular weights. Thus, the HA can have a molecular weight as low as $5 \times 10^4$ and ranging up to as high as $5 \times 10^6$ as described in the parent application. As in the parent application, the molecular weight of the Polyox can, of course, range from about 1 to $5 \times 10^6$; however, it has also been found that when using the lower molecular weight HA (within the above range of $5 \times 10^4$ to $5 \times 10^6$), one can use a Polyox with a molecular weight as low as $1 \times 10^5$.

In addition, it has also been discovered that compositions having the desired properties can also be obtained using hylan instead of a hyaluronate. Hylan is a chemically modified substance obtained from a hyaluronate and is described in detail and claimed in co-pending application Ser. No. 710,929, filed Mar. 12, 1985 now U.S. Pat. No. 4,713,448. Moreover, as described in co-pending application Ser. No. 804,178, filed Nov. 29, 1985, now abandoned, the term "hyaluronan" is increasingly being used in the literature in place of the traditional hyaluronic acid and may be used interchangeably therewith. The contents of both such applications are incorporated herein by reference.

Accordingly, the present invention provides, in one aspect thereof, water based, viscoelastic compositions comprising a mixture of a hyaluronate (i.e., a hyaluronan), preferably an alkali metal or alkaline earth metal hyaluronate, and most preferably sodium hyaluronate having a molecular weight of about $5 \times 10^4$ to about $5 \times 10^6$; or a hylan and a poly(ethylene oxide) having a molecular weight of about $1 \times 10^5$ to about $5 \times 10^6$.

In another aspect, the invention provides cosmetic formulations comprising the composition in admixture with other, conventional additives used in cosmetics, including surfactants, thickeners, moisturizing agents, fibers, pigments and dyes and fragrances.

DETAILED DESCRIPTION OF THE INVENTION

As noted above, and in parent application Ser. No. 619,534, filed Jun. 11, 1984, now abandoned, the invention provides highly viscoelastic compositions comprising a mixture of a hyaluronate and a poly(ethylene oxide). Generally speaking, hyaluronates are more viscous than poly(ethylene oxides) and poly(ethylene oxides) are more elastic than hyaluronates. Moreover, suitable hyaluronates are quite expensive to produce. Notwithstanding the teaching in prior art U.S. Pat. No. 3,387,061, we have found that when a composition according to the invention is produced, the result is a water soluble product having the desirable properties of both the hyaluronate and the poly(ethylene oxide) at a much reduced cost.

In accordance with the original invention described and claimed in the parent application, as the hyaluronic acid salt there can be used a pure HA salt, for example, an alkali or alkaline earth metal salt; or a mixture of hyaluronates containing proteins and other naturally occurring substances, such as the product described in U.S. Pat. No. 4,303,676, the contents of which are incorporated herein by reference. Generally, the hyaluronate used in the invention will have a molecular weight in the range of about $1 \times 10^6 - 5 \times 10^6$.

The poly(ethylene oxide) can be any water soluble linear homopolymer of ethylene oxide having a molecular weight of about $1 \times 10^6 - 5 \times 10^6$. Such poly(ethylene oxides) are available from Union Carbide Corporation (Polyox ® brand) and a particularly suitable grade of Polyox ® is that which is identified as "Polyox ® Coagulant" in the Union Carbide Corporation publication entitled "Polyox ®—Water Soluble Resins are Unique" ©1967, 1972, 1973, 1978, 1981 by Union Carbide Corporation. The poly(ethylene oxide) has an average molecular weight of $5 \times 10^6$ and a viscosity (1% solution) of 4,500–6,500 cps at 25° C. The relative concentration of each of the components in the mixture can be from 0.01 to 2%. The ratio hyaluronate:poly(ethylene oxide) in the mixture can be from 1:50 to 100:1 by weight.

In accordance with the improvement which is the subject matter of this application, the HA salt can have a molecular weight as low as about 50,000 and ranging up to the upper limit of the invention described in the parent application, i.e. about $5 \times 10^6$.

The poly(ethylene oxide) with which this improvement is concerned, will have a molecular weight typically in the same range as in the parent application, i.e., $1 - 5 \times 10^6$; however, we have also discovered that with a relatively low molecular weight HA, one can also use a lower molecular weight poly(ethylene oxide), i.e., on the order of $1 \times 10^5$.

Cosmetic formulations according to the invention can be made containing widely varying amounts of the aforesaid mixtures, i.e., from 0.1 up to about 50% of a hyaluronate-poly(ethylene oxide) mixture depending on the nature of the cosmetic product and the performance characteristics desired by such formulation. Again, depending upon the type of formulation, it will contain various cosmetic ingredients such as emollients, sugar alcohols, neutral or anionic polysaccharides, preservatives (which do not react with or degrade the hyaluronate), fragrences, water and the like. These latter materials are all conventional in the art and well known to cosmetic chemists. Included among the cosmetic formulations are moisturizing creams and lotions, shampoos, liquid soaps, shaving cream, eye cream, lip protective creams and make-up, as well as eye drops.

EXAMPLES

The invention will now be described in greater detail in the following examples which are illustrative of the invention without, however, being a limitation thereof.

EXAMPLE 1

A 1% aqueous solution of Polyox ® coagulant (molecular weight about 5,000,000, Union Carbide Corporation) was mixed with BIOMATRIX ™ sodium hyaluronate (0.5% water solution of sodium hyaluronate, which includes large amounts of proteins, molecular weight about 2,000,000) and water in such proportions to obtain a mixture which contains 0.5% of poly(ethylene oxide) and 0.05% of sodium hyaluronate. The specific viscosity $\eta sp$ of the mixture was 451. The individual specific viscosities of an 0.5% hyaluronate were 100 and 11, respectively. Thus, the additive value for the mixture of the two is 111, whereas the real or actual value of $\eta sp$ for the mixture is about four times greater than the additive value which would be expected.

EXAMPLE 2-5

The above example was repeated with different mixtures having different hyaluronate/poly(ethylene oxide) ratios. The specific viscosities of the mixtures of the solutions of poly(ethylene oxide) and sodium hyaluronate of the corresponding concentrations, and also, the calculated additive values are presented in FIG. 1. They are also set forth in Table I.

TABLE I

| Example | | Specific Viscosity | |
| --- | --- | --- | --- |
| | — | additive value | actual value |
| 1 NaHA | 11 | 111 | 451 |
| Polyox | 100 | | |
| 2 NaHA | 12.5 | 54.5 | 250 |
| Polyox | 42 | | |
| 3 NaHA | 15 | 35 | 137.5 |
| Polyox | 20 | | |
| 4 NaHA | 15 | 225 | 70 |
| Polyox | 7.5 | | |
| 5 NaHA | 17.5 | 20 | 37.5 |

TABLE I-continued

| Example | Specific Viscosity | |
|---|---|---|
| | additive value | actual value |
| Polyox | 2.5 | |

From these data it can be seen that the real value for each mixture is substantially greater than the calculated or additive value.

EXAMPLE 6

Figure 2:
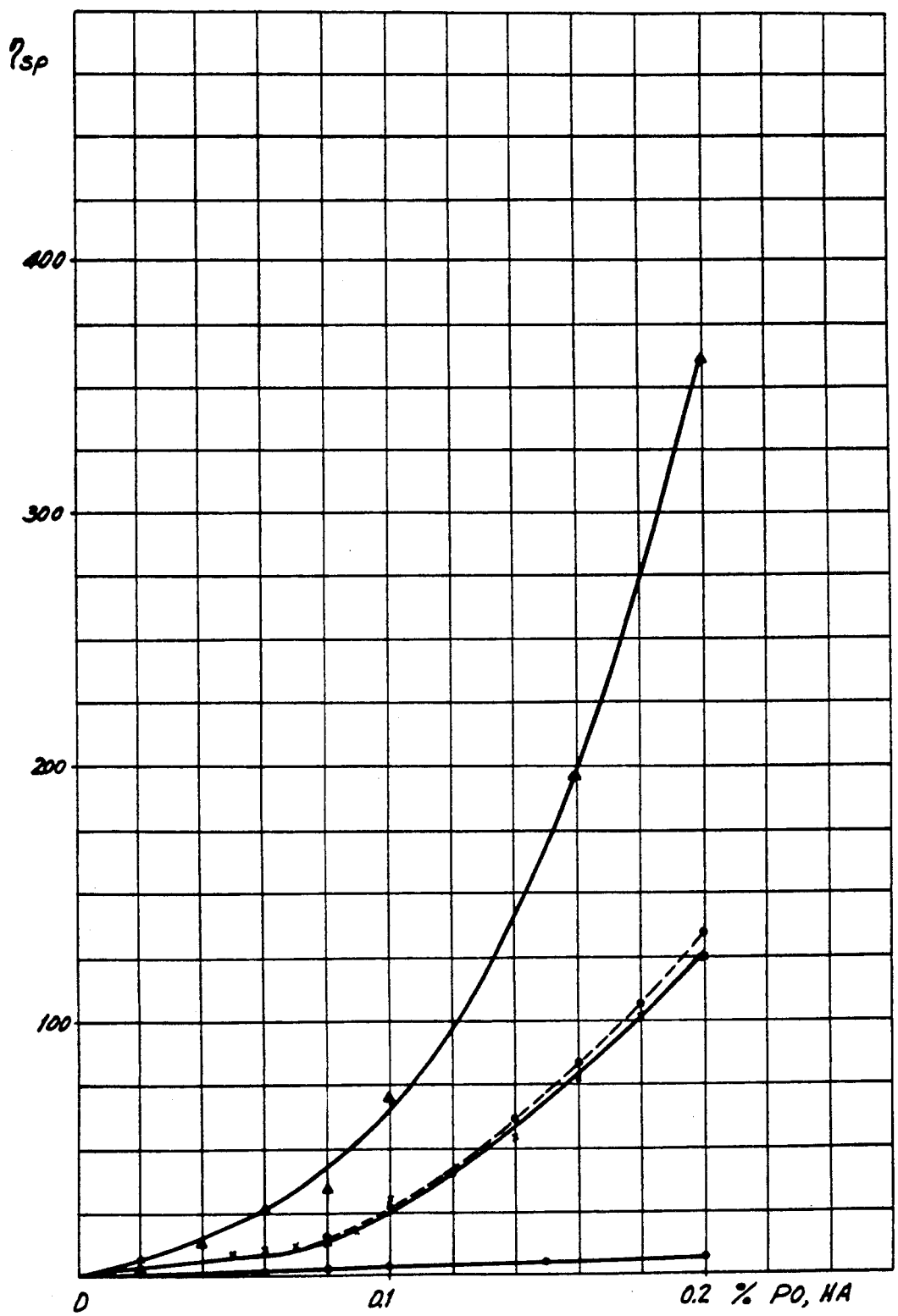
FIG. 2 is a graph showing the specific viscosity of an aqueous solution of 1:1 mixture of poly(ethylene oxide) and sodium hyaluronate at differing polymer concentrations (example 6).

Several mixtures were prepared from a 1% water solution of Polyox ® coagulant and BIOMATRIX TM sodium hyaluronate with the ratio of two polymers being 1:1 and with different concentrations of polymers in the mixtures. The $\eta$sp values are plotted in FIG. 2 against polymer concentrations. For these mixtures the measured values of $\eta$sp are seen to be substantially greater than the additive values.

EXAMPLE 7

A 1% water solution of Polyox ® coagulant and Hyladerm ® (1% water solution of sodium hyaluronate, protein content 0.01%, molecular weight 4,000,000, Biomatrix, Inc.) were mixed with water in such a proportion that the resulting mixture contains 0.05% of each polymer. The $\eta$sp of the mixture was 91. The specific viscosity of the poly(ethylene oxide) and sodium hyaluronate solutions of corresponding concentrations were, respectively, 1.8 and 39. The additive value thus is 40.8 which is less than half of the actual value for the mixture.

In the following examples (8-27), the data for which appears in Table II, three different samples of sodium hyaluronate were used. The molecular weight of the samples were about $5 \times 10^4$, $2.5 \times 10^5$ and $8 \times 10^5$. These samples were obtained by a conventional hydrolysis of high molecular weight sodium hyaluronate recovered from rooster combs. Three different samples of Polyox ® were also used in these examples. The molecular weight of these samples were $5 \times 10^6$, $9 \times 10^5$ and $1 \times 10^5$. Rheological measurements were done using a Bohlin Rheometer at 25° C. The following parameters were measured: shear viscosity at shear rate ($\gamma$) 1,95[1], dynamic viscosity at frequency of 5 Hz and dynamic storage modulus at frequency of 5 Hz.

RHEOLOGICAL PROPERTIES OF SODIUM HYALURONATE - POLY(ETHYLENE OXIDE) MIXTURES

| | Mixture composition, mg/ml | | Rhelogical properties | | | | | |
|---|---|---|---|---|---|---|---|---|
| | Sodium hyaluronate MW/concentration or | Poly(ethylene oxide) | Shear viscosity at $\gamma 1.9\ s^{-1}$, cPs | | Dynamic viscosity at 5 Hz, cPs | | Storage modulus at 5 Hz, Pa | |
| Example # | hylan mw/concentration* | MW/concentration | found | additive | found | additive | found | additive |
| 8 | 50,000/5 | — | 5.04 | — | 1.28 | — | 0.094 | — |
| 9 | — | 5,000,000/5 | 401.00 | — | 18.10 | — | 1.160 | — |
| 10 | 50,000/5 | 5,000,000/5 | 653.00 | 406.04 | 52.50 | 19.38 | 1.790 | 1.254 |
| 11 | — | 900,000/10 | 33.30 | — | 18.30 | — | 0.324 | — |
| 12 | 50,000/5 | 900,000/10 | 309.00 | 38.34 | 52.70 | 19.58 | 0.595 | 0.418 |
| 13 | — | 100,000/15 | 8.87 | — | 1.36 | — | 0.134 | — |
| 14 | 50,000/5 | 100,000/15 | 23.00 | 13.91 | 2.87 | 2.64 | 0.221 | 0.228 |
| 15 | — | 5,000,000/8 | 991.00 | — | 96.10 | — | 4.600 | |
| 16 | 250,000/2 | — | 21.90 | — | 1.02 | — | 0.139 | — |
| 17 | 250,000/2 | 5,000,000/8 | 1,260.00 | 1012.90 | 115.00 | 97.12 | 4.430 | 4.739 |
| 18 | 250,000/5 | — | 31.40 | — | 3.78 | — | 0.211 | — |
| 19 | 250,000/5 | 5,000,000/5 | 690.00 | 431.40 | 76.00 | 21.88 | 2.490 | 1.371 |
| 20 | 250,000/5 | 900,000/10 | 231.00 | 64.70 | 71.70 | 22.08 | 0.657 | 0.534 |
| 21 | 250,000/5 | 100,000/15 | 27.20 | 40.27 | 10.70 | 5.14 | 0.342 | 0.806 |
| 22 | 800,000/5 | — | 180.00 | — | 72.40 | — | 1.540 | — |
| 23 | 800,000/5 | 5,000,000/5 | 2,810.00 | 581.00 | 272.00 | 90.50 | 12.100 | 2.700 |
| 24 | 800,000/5 | 900,000/10 | 1,240.00 | 213.30 | 303.00 | 90.70 | 7.420 | 1.864 |
| 25 | 800,000/2 | — | 70.00 | — | 23.90 | — | 0.273 | — |
| 26 | 800,000/2 | 5,000,000/8 | 2,720.00 | 1,061.00 | 236.00 | 120.00 | 12.500 | 4.873 |
| 27 | 800,000/5 | 100,000/15 | 451.00 | 188.87 | 90.40 | 73.76 | 1.870 | 1.674 |

*In examples 22-27, the substance used is hylan and not hyaluronate.

The following can be concluded from the experimental data in Table II:

(1) All measured (actual) rheological parameters for sodium hyaluronate-poly(ethylene oxide) combinations are higher than the additive values calculated from the data for solutions of each of the components separately.

(2) Shear and dynamic viscosities are more sensitive parameters than are storage modulus.

(3) The degree of interaction between the two polymers does not depend only on the molecular weight of sodium hyaluronate.

(4) The degree of interaction seems to decrease with a decrease in the molecular weight of the Polyox. Compare, e.g., examples 23 and 27.

The following examples (28 and 29) are directed, respectively, to a shaving cream and a moisturizing eye cream.

EXAMPLE 28

A shaving gel formulation as set forth below was prepared.

| | % by weight |
|---|---|
| Sodium hyaluronate, 1% solution (Hyladerm ®, Biomatrix, Inc.) | 2.56 |
| Poly(ethylene oxide), 1% solution (Polyox ® coagulant) | 0.36 |
| Polyacrylic acid (thickener) (Carbopol 940 ®, B.F. Goodrich) | 0.41 |
| Triethanolamine | 0.41 |
| Hydroxyethylcellulose, 1% solution (Cellosize ®, Union Carbide Corporation) | 8.2 |
| Squalene Robane ®, Robeco Chemicals, Inc.) | |
| Coconut oil (Cochin ®, Acme-Hardesty Co., Inc.) | 0.31 |
| Preservative | 0.26 |
| Fragrance | 0.26 |

|  | % by weight |
|---|---|
| Water | 87.0 |

To prepare this formulation, the Carbopol resin was dispersed in water, after which all the other components but triethanolamine were added with stirring. Then the triethanolamine was stirred in. The formulation obtained is a translucent, viscous gel-like mixture. When tested as a shaving gel it gave very good results by providing a smooth and clean shave. Furthermore, this shaving gel provided moisturizing action and could be left on the skin after shaving.

EXAMPLE 29

This example illustrates a moisturizing eye gel.

|  | % by weight |
|---|---|
| A. Hyladerm ® | 2.0 |
| Polyox ®, 1% water solution | 0.4 |
| Carbopol ® 940 | 0.4 |
| Water | 90.9 |
| B. Liponic ® EG-1 (Lipo Chemicals, Inc.) | 0.5 |
| Volpo ® - 5 (Croda, Inc.) | 1.0 |
| Solulan ® C-24 (Amerchol Co.) | 1.0 |
| Crodafos ® N3 neutral (Croda, Inc.) | 0.8 |
| Robane ® | 1.0 |
| Crodamol ® PMP (Croda, Inc.) | 0.5 |
| Glucam ® E-10 (Amerchol Co.) | 0.7 |
| Preservative | 0.3 |
| C. Triethanolamine | 0.4 |
| Fragrance | 0.1 |

This formulation is prepared in separate stages as follows:

Part A of the mixture was prepared by dispersing the Carbopol in water and then stirring in the other components. All the Part B components were mixed together and heated to 70° C. Parts A and B were then combined and the triethanolamine and fragrance were added. The resulting cream was stable and smooth and had good moisturizing qualities and an excellent feel on the skin.

The following examples 30-31 illustrate, respectively, formulation for a moisturizing hand lotion and an emollient moisturizing cream.

EXAMPLE 30

|  | parts by weight |
|---|---|
| Hyladerm ® | 2.5 |
| Polyox ®, 1% water solution | 0.3 |
| Glycerine | 5.0 |
| Ethyl alcohol | 15.0 |
| Oleth-5 | 2.0 |
| (Lipocol ® 0-5, Lipo Chemicals, Inc.) |  |
| Glucam ® E-10 | 0.7 |
| Preservative | 0.3 |
| Fragrance | 0.15 |
| Water up to | 100.00 |

The formulation was prepared by mixing all the components together.

EXAMPLE 31

|  | parts by weight |
|---|---|
| A. Hyladerm ® | 2.5 |
| Polyox ®, 1% water solution | 1.5 |
| Carbopol ® 940 | 0.5 |
| Water | 83.5 |
| B. Petrolatum | 5.0 |
| Robane ® | 2.0 |
| Lanoxide ® 59 | 2.5 |
| Silicone Copolymer ® F-754 | 1.5 |
| Preservative | 0.3 |
| C. Triethanolamine | 0.5 |
| Fragrance | 0.1 |

This formulation was prepared in separate stages as described in example 29. The resulting cream was rich with excellent moisturizing qualities and did not give a greasy feeling on the skin.

The invention also includes within its scope eye drop formulations, including both eye drop formulations containing one or more preservatives to ensure stability of the formulation in an already opened container of the product as well as eye drop formulations in single dose forms without preservative. Such non-preservative containing formulations are desirable because certain users have eyes that are sensitive to the commonly used preservatives. Such formulations according to the invention are feasible because as a result of the very low protein content of the hyaluronate used, the formulation will not support the growth of most microorganisms and, therefore, the need for preservatives is avoided.

The following examples 32 and 33 illustrate, respectively, eye drop formulations with and without preservatives.

EXAMPLE 32

|  | parts by weight |
|---|---|
| Hyladerm ® | 2.00 |
| Polyox ®, 1% water solution | 2.20 |
| Benzalkonium chloride | 0.01 |
| Disodium edetate | 0.05 |
| Water up to | 100.00 |

The formulation, when applied into an eye, gives a very comfortable feeling.

EXAMPLE 33

|  | parts by weight |
|---|---|
| Hyladerm ® | 0.45 |
| Polyox ®, 1% water solution | 0.20 |
| Water up to | 100.00 |

EXAMPLE 34

Single Dose Non-Preserved Eye Drop

The formulation of example 33 which does not contain a preservative was packed in 0.2 ml sterile plastic containers and used as eye drops for a single application. The amount can vary from about 0.1–0.5 ml, but 0.2 ml is the preferred amount.

Certain ingredients set forth in the formulations of examples 28-33 are identified by trademarks. The following is a list of the chemical names of these ingredients.

| Liponic ® Eg-1 | Glycereth-26 (polyethylene ether of glycerin) |
|---|---|
| Volpo-5 ® | Oleth-5 (polyethylene glycol |

| | -continued |
|---|---|
| | ether of oleyl alcohol) |
| Solulan ® C-24 | Choleth-24 (polyethylene glycol ether of Cholesterol) |
| Crodafos ® N3 neutral | DEA-Oleth-3 Phosphate (disthanolamine salt of a complex mixture of esters of phosphoric acid and Oleth-3) |
| Crodamol ® PMP | (propoxylated myristyl propionate) PPG-3 Myristyl Ether Propionate) |
| Glucam ® E-10 | Methyl gluceth-10 (polyethylene glycol ether of methyl glucose) |
| Lanoxide ® | Polyoxyethylene glycol ether of stearic acid, Lanaetex Products, Inc. |

Variations and modifications can, of course, be made without departing from the spirit and scope of the invention.

Having thus described our invention what we desire to secure by Letters Patent and hereby claim is:

1. In a water based viscoelastic composition comprising a mixture of a hyaluronate and a polymer in water, the improvement wherein the hyaluronate has a molecular weight of about 50,000 to about 5,000,000 and the polymer is a water-soluble poly(ethylene oxide), which is a linear homopolymer of ethylene oxide having a molecular weight of about $1 \times 10^5$ to about $5 \times 10^6$; with the proviso that when the polymer has a molecular weight of about $1 \times 10^5$, the hyaluronate has a molecular weight of not more than about $1 \times 10^6$.

2. A composition according to claim 1 wherein the hyaluronate is an alkali metal or alkaline earth metal hyaluronate.

3. A composition according to claim 2 wherein the hyaluronate is sodium hyaluronate.

4. A composition according to claim 2 wherein the hyaluronate is a pure hyaluronic acid salt or a mixture of hyaluronates with proteins and other naturally occurring substances derived from the natural material from which the hyaluronate is derived.

5. A composition according to claim 1 wherein the concentration of each component of the mixture is from about 0.01% to about 2% and the ratio by weight of the hyaluronate to the poly(ethylene oxide) is about 1:50 to 100:1.

6. A composition according to claim 1 wherein the molecular weight of the hyaluronate is about 50,000 to about 1,000,000 and the molecular weight of the linear homopolymer of ethylene oxide is about $1 \times 10^5$ to about $5 \times 10^6$.

7. An ophthalmic formulation comprising from about 0.1 to about 50% by weight of composition according to claim 1 which is an eye drop formulation and further comprising an effective amount of at least one preservative.

8. A single dose of the eye drop formulation according to claim 7 comprising about 0.1-0.5 ml of said formulation in a sealed, sterile container therefor.

* * * * *